United States Patent [19]

Kondo et al.

[11] Patent Number: 4,876,404

[45] Date of Patent: Oct. 24, 1989

[54] PREPARATION OF DICHLOROTRIFLUOROMETHYLTOLUENES INCLUDING NOVEL ISOMERS

[75] Inventors: Takeshi Kondo, Sayama; Toshikazu Kawai, Kawagoe; Hideki Oshio, Omiya, all of Japan

[73] Assignee: Central Glass Company, Limited, Ube, Japan

[21] Appl. No.: 84,019

[22] Filed: Aug. 11, 1987

[30] Foreign Application Priority Data

Aug. 13, 1986 [JP] Japan ................................ 61-188575
Apr. 30, 1987 [JP] Japan ................................ 62-106570

[51] Int. Cl.[4] .................... C07C 17/20; C07C 17/24; C07C 17/32; C07C 21/24
[52] U.S. Cl. .................................. 570/145; 564/417; 568/938; 570/127; 570/184; 570/194
[58] Field of Search ............................... 570/145, 194

[56] References Cited

U.S. PATENT DOCUMENTS

| 3,297,771 | 1/1967 | Leebrick et al. | 570/194 |
| 3,966,832 | 6/1976 | Lademann et al. | 570/145 |
| 4,080,392 | 3/1978 | Ryf | 570/145 |
| 4,129,602 | 12/1978 | Sendlak | 570/145 |
| 4,462,937 | 7/1984 | Ramanadin et al. | 570/145 |

OTHER PUBLICATIONS

"A New Method For the Trifluoromethylation of Aromatics", by A. Marhold et al., Journal of Fluorine Chemistry, 18 (1981), pp. 281–291.

*Primary Examiner*—J. E. Evans
*Attorney, Agent, or Firm*—Fleit, Jacobson, Cohn, Price, Holman & Stern

[57] ABSTRACT

Dichlorotrifluoromethyltoluenes useful in producing some medicines and agricultural chemicals are formed with good yields by reacting dichlorotrichloromethyltoluenes with hydrogen fluoride usually at 0°–100° C. under pressure of 3–20 kg/cm$^2$. Besides known 3,4-dichloro-6-trifluoromethyltoluene and 3,4-dichloro-5-trifluoromethyltoluene, novel isomers are also obtained by this method.

6 Claims, No Drawings

PREPARATION OF DICHLOROTRIFLUOROMETHYLTOLUENES INCLUDING NOVEL ISOMERS

BACKGROUND OF THE INVENTION

This invention relates to novel isomers of 3,4-dichloro-6-trifluoromethyltoluene, which is a known compound, and a method of preparing known and novel dichlorotrifluoromethyltoluenes. These isomeric compounds are useful as materials of some medicines and agricultural chemicals, and particularly as the materials of aminotrifluoromethyltoluenes (or methylaminobenzotrifluorides) which are of use as intermediates of some medicines such as tranquilizers and antiphlogistic anodynes and agricultural chemicals represented by herbicides.

It is known that 3,4-dichloro-6-trifluoromethyltoluene can be formed by the following reaction. (J. Fluor. Chem. (1981), 281-291)

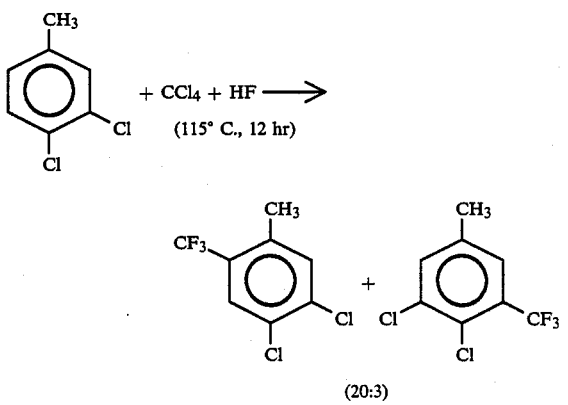

(20:3)

However, in this process the conversion of 3,4-dichlorotoluene is only about 25%, and it is not easy to separate by-produced 3,4-dichloro-5-trifluoromethyltoluene. Besides, some portions of hydrogen fluoride and carbon tetrachloride react with each other to form trichlorofluoromethane as a by-product. We are aware of no literature showing dichlorotrifluoromethyltoluenes other than the above indicated two isomers.

SUMMARY OF THE INVENTION

It is an object of the present invention to provide a more favorable method of preparing dichlorotrifluoromethyltoluenes.

It is another object of the invention to provide novel dichlorotrifluoromethyltoluenes.

According to the invention there is provided a method of preparing a dichlorotrifluoromethyltoluene (abbreviated to DCTFT), characterized in that a dichlorotrichloromethltoluene (abbreviated to DCTCT) is reacted with hydrogen fluoride.

By this method a desired DCTFT can easily be prepared with good Yield.

DCTFT's that can be formed by this method include novel isomers such as 2,3-dichloro-4-trifluoromethyltoluene, 2,3-dichloro-6-trifluoromethyltoluene, 2,4-dichloro-5-trifluoromethyltoluene, 2,5-dichloro-4-trifluoromethyltoluene and 2,6-dichloro-3-trifluoromethyltoluene.

DETAILED DESCRIPTION OF THE INVENTION

The reaction according to the invention for fluorinating a DCTCT is carried out in an autoclave made of a corrosion resistant material such as a Mo-containing stainless steel by using hydrogen fluoride in a quantity not less than the theoretical quantity at a temperature in the range from 0° to 150° C., and preferably from room temperature to 100° C. This reaction is carried out under a pressure of 3–20 kg/cm$^2$, and preferably 8–10 kg/cm$^2$. It is suitable to use 3.2 to 12 mols, and preferably 6 to 9 mols, of hydrogen fluoride per 1 mol of DCTCT.

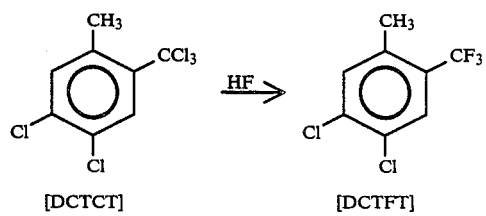

[DCTCT]     [DCTFT]

The reaction time is usually 3–6 hr though it is variable depending on some factors. After the fluorination reaction, a high purity DCTFT can easily be recovered by first washing the reaction product with an aqueous alkali solution for removal of unreacted hydrogen fluoride and subjecting the washed product to distillation under reduced pressure for separation from solvent and by-products having higher boiling points.

As to preparation of the starting material in this invention, we prefer preparing a DCTCT from a corresponding dichlorotoluene. More particularly, a DCTCT is easily formed by reaction between a dichlorotoluene and carbon tetrachloride in the presence of an aluminum halide. In this reaction 1 to 10 mols of carbon tetrachloride is used per 1 mol of dichlorotoluene, and it is possible to use carbon tetrachloride also as a liquid medium for the reaction. Typical examples of the aluminum halide used in this reaction are anhydrous aluminum chloride and anhydrous aluminum bromide. The quantity of the aluminum halide is 1 to 6 mols, and preferably 1 to 3 mols, per 1 mol of dichlorotoluene. The aluminum halide combines with the DCTCT formed by the reaction to form a complex represented by the following formula.

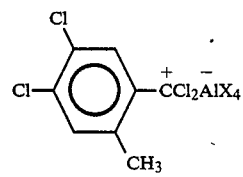

In case of shortage of the aluminum halide, there is selectively formed a dichlorobis(dichloromethylphenyl)methane (abbreviated to DCBM) represented by the following formula as a by-product. On the other hand, selectivity of the reaction to DCTCT does not significantly augment even if an excessively large quantity of aluminum halide is used.

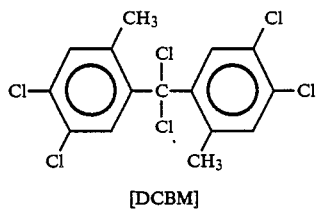

[DCBM]

This reaction is carried out at a temperature in the range from 0° to 100° C., and preferably from 20° to 80° C. The reaction time is usually from 20 min to 4 hr though it is widely variable. In this reaction it is preferable to use an organic solvent selected from, for example, dichloromethane, chloroethanes and chlorofluoroethanes. The best solvent is 1,2-dichloroethane by which the selectivity to DCTCT is remarkably enhanced. After the reaction the aforementioned complex is decomposed to thereby obtain DCTCT by mixing the reaction product with water.

As disclosed in our copending patent application Ser. No. 07/084,020, filed Aug. 11, 1987, now abandoned, nitration of DCTFT's obtained by the present invention with fuming nitric acid in the presence of concentrated sulfuric acid gives novel isomeric compounds named dichlorotrifluoromethylnitrotoluenes (DCTFNT), and aminotrifluoromethyltoluenes (ATFT) useful as intermediates of medicines and agricultural chemicals are obtained with good Yields by reaction between DCTFNT's and hydrogen in the presence of a hydrogenation catalyst and an acid acceptor such as, for example, sodium hydroxide.

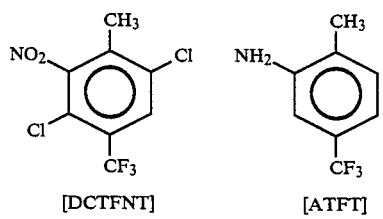

[DCTFNT]  [ATFT]

The invention is further illustrated by the following nonlimitative examples.

EXAMPLE 1A

A mixture of 27.0 g (0.203 mol) of anhydrous aluminum chloride and 100.0 g of carbon tetrachloride was kept stirred, and a solution of 16.1 g (0.1 mol) of 3,4-dichlorotoluene in 54 g of carbon tetrachloride was dropped into the mixture in a total period of 2 hr while the temperature of the reaction system was maintained at 50°–52° C. The total quantity of carbon tetrachloride reached 1.0 mol. After that stirring of the reaction system was continued for 2 hr, and thereafter the reaction liquid was left to cool down. Then the reaction liquid was poured into 700 ml of iced water, followed by stirring at room temperature. After removing aluminum chloride, an organic phase was extracted from the aqueous liquid with carbon tetrachloride. The organic phase was washed with 5% aqueous solution of sodium hydroxide, followed by drying with anhydrous calcium chloride, and the solvent was dissipated by distillation under reduced pressure. As the result 25.2 g of crude DCTCT was obtained. By gas chromatography the crude product was proved to contain 73.3 wt % (Yield 66.3%) of 3,4-dichloro-6-trichloro-methyltoluene, referred to as DCTCT-(1), and 16.2 wt % (Yield 20.3%) of DCBM, while neither unreacted dichlorotoluene nor 3,4-dichlorobis(trichloromethyl)-toluene was detected.

The whole quantity (25.2 g) of the crude DCTCT and 10.9 g of hydrogen fluoride were charged in a 100 ml autoclave, and these reactants were stirred and kept heated at 60°–80° C., while the pressure in the autoclave was kept at 8 kg/cm2 by continuously extracting hydrogen chloride gas formed as a by-product of the reaction from the top of reflux tower by means of a primary pressure regulating valve. After the lapse of 3 hr the pressure in the autoclave was no longer rising, so that it was decided that the fluorinating reaction had been completed. Then the reaction product was taken out of the autoclave and washed with 10% aqueous solution of sodium hydroxide to remove unreacted hydrogen fluoride, followed by distillation under reduced pressure. The thus treated product was !2.82 g (0.0550 mol, yield 55.0%) of 3,4-dichloro-6-trifluoromethyltoluene (purity 98.2%, boiling point 97°–100° C. at 23 mmHg).

EXAMPLE 1B

The process of Example 1A was repeated except that the initial step was modified to dropping of a solution of 16.1 g (0.1 mol) of 3,4-dichlorotoluene in 19.1 g of 1,2-dichloroethane into a mixture of 27.0 g (0.203 mol) of anhydrous aluminum chloride, 31.5 g (0.205 mol) of carbon tetrachloride and 50.5 g of 1,2-dichloroethane. In this case the final product was 15.18 g (0.065 mol, Yield 65.3%) of 3,4-dichloro-6-trifluoromethyltoluene of which purity was 98.5%.

EXAMPLE 2

As a first run, the synthesis of DCTCT was performed in the same manner as in Example 1A except that 16.1 g (0.1 mol) of 2,3-dichlorotoluene was used in place of 3,4-dichlorotoluene in Example 1A. As the result 24.5 9 of crude DCTCT was obtained. By gas chromatography the crude product was proved to contain 42.8 wt % (Yield 37.6%) of 2,3-dichloro-4-trichloromethyltoluene, referred to as DCTCT-(2), 27.i wt % (Yield 23.8%) of 2,3-dichloro-6-trichloromethyltoluene, referred to as DCTCT-(3), and 30.1 wt % (yield 36.6%) of DCBM, while unreacted dichlorotoluene was not detected. The crude product was dissolved in 50 ml of n-hexane to remove insoluble matter, and the filtrate was subjected to concentration under reduced pressure and distillation under reduced pressure to thereby obtain 10.5 g (0.0377 mol, yield 37.7%) of 99.2% purity mixture of DCTCT-(2) and DCTCT-(3). BY gas chromatography, 0.15 g of DCTCT-(2) (purity 99.5%, boiling point 120°–125° C. at 3 mmHg and 0.12 g of DCTCT-(3) (purity 99.0%, boiling point 109°–115° C. at 3 mmHg) were separated from the mixture. The structure of DCTCT-(2) was confirmed by mass spectroscopy (MASS) (M+276) and H-NMR (in CDCl3, δ2.80 3H (CH ) s, 7.99 1H (4-H) s, 7.38 1H (6-H) s). The structure of DCTCT-(3) was confirmed by mass spectroscopy (MASS) (M+276) and H-NMR (in CDCl3. δ2.47 3H (CH3) s, 7.221H (4-H) s, 7.90 1H (5-H) s).

In a second run of synthesis of DCTCT, a mixture of 108 g (0.812 mol) of anhydrous aluminum chloride, 125 g (0.812 mol) of carbon tetrachloride and 205 g of 1,2-dichloroethane was kept stirred, and a solution of 65.4 g (0.406 mol) of 2,3-dichlorotoluene in 78.0 g of 1,2-dichloroethane was dropped into the mixture in a total period of 30 min while the temperature of the reaction system was maintained at 50°-52° C. After that stirring of the reaction system was continued for 2 hr, and thereafter the reaction liquid was left to cool down. Then the reaction liquid was poured into 1000 ml of iced water, followed by stirring at room temperature. After removing aluminum chloride, the organic phase was treated in the same manner as in Example 1A. As the result 102 g of crude DCTCT was obtained. By gas chromatography the crude product was proved to contain 42.8 wt % (Yield 37.6%) of DCTCT-(2), 27.1 wt % (Yield 23.8%) of DCTCT-(3) and 30.1 wt % (Yield 36.6%) of DCBM, while unreacted 2,3-dichlorotoluene was not detected.

The whole quantity (102 g) of the crude DCTCT obtained by the above second run and 109 g of hydrogen fluoride were charged in a 300 ml stainless steel autoclave, and these reactants were stirred and kept heated at 95°-100° C. The pressure in the autoclave was kept at about 8 kg/cm2 by continuously extracting hydrogen chloride gas in the same manner as in Example 1A. After the lapse of about 3 hr the pressure in the autoclave was no longer rising, so that the fluorinating reaction was terminated. The reaction product was washed with aqueous solution of sodium hydroxide to remove unreacted hydrogen fluoride, followed by distillation under reduced Pressure. The thus treated product was a mixture of 7.42 9 (0.0319 mol, yield 16.6%) of 2,3-dichloro-4-trifluoromethyltoluene (purity 98.3%, boiling point 115°-118° C. at 35 mmHg), referred to as DCTFT-(2), and 7.45 g (0.0323 mol, Yield 28.3%) of 2,3-dichloro-6-trifluoromethyltoluene (purity 99.2%, boiling point 108°-110° C. at 35 mmHg), referred to as DCTFT-(3). The structure of DCTFT-(2) was confirmed by MASS (M+228), H-NMR (in CDCl$_3$, δ2.48 3H (CH$_3$) s, 7.24 1H (6-H) s, 7.521H (5-H) s) and F-NMR (in CDCl$_3$, 61.5 ppm 3F (CF$_3$) s, standard substance was CFCl$_3$). The structure of DCTFT-(3) was confirmed by MASS (M+228), H-NMR (in CDCl$_3$, δ2.58 3H (CH$_3$) s, 7.48 2H (4,5-H) s, 7.521H (5-H) s) and F-NMR (in CDCl$_3$, 63.3 ppm 3F (CF$_3$) s, standard substance was CFCl$_3$)

EXAMPLE 3

As a first run, the synthesis of DCTCT was performed in the same manner as in Example IA except that 16.1 g (0.1 mol) of 2,4-dichlorotoluene was used in place of 3,4-dichlorotoluene in Example 1A. As the result 24.3 9 of crude DCTCT was obtained. By gas chromatography the crude product was proved to contain 70.2 wt % (Yield 61.3%) of 2,4-dichloro-5-trichloromethyltoluene, referred to as DCTCT-(4), and 29.8 wt % (Yield 35.9%) of DCBM, while unreacted dichlorotoluene was not detected. The crude product was dissolved in 50 ml of n-hexane to remove insoluble matter, and the filtrate was subjected to concentration under reduced pressure and distillation under reduced pressure to thereby obtain 13.8 g (0.0496 mol, Yield 49.6%) of DCTCT-(4) (purity 98.7%, melting point 79.0°-80.2° C.) The structure of DCTCT(4) was confirmed by MASS (M+276) and H-NMR (in CDC$_{13}$, δ2.60 3H (CH3) s, 7.22 1H (6-H) s, 8.21 1H (3-H) s).

As a second run of synthesis of DCTCT-(4), the first step of Example 1B (using 1,2-dichloroethane) was repeated except that 16.1 g (0.1 mol) of 2,4-dichlorotoluene was used in place of 3,4-dichlorotoluene in Example 1B. As the result 24.3 g of crude DCTCT-(4) (purity 70.2%, yield 61.3%) was obtained. In this product unreacted dichlorotoluene was not detected, and only DCBM was detected as by-product.

Next, 24.3 g of the crude DCTCT-(4) obtained by the above first run and 10.0 g of hydrogen fluoride were subjected to reaction in the same manner as in Example 1A except that the reaction temperature was raised to 95°-102° C. The reaction product was washed with aqueous solution of sodium hydroxide to remove unreacted hydrogen fluoride and then subjected to distillation under reduced pressure. As the result 12.3 g (0.0527 mol, Yield 86.0%) of 2,4-dichloro-5-trifluoromethyltoluene (purity 98.2%, boiling point 83°-85° C. at 6 mmHg), referred to as DCTFT-(4), was obtained. The structure of this compound was confirmed by MASS (M+228), H-NMR (in CDCl$_3$, δ2.36 3H (CH$_3$) s, 7.43 1H (6-H) s, 7.50 1H (3-H) s) and F-NMR (in CDCl$_3$ 62.8 ppm 3F (CF$_3$) s, standard substance was CFCl ).

EXAMPLE 4

As a first run, the initial process (preparation of DCTCT) in Example 1A was repeated except that 16.1 g (0.1 mol) of 2,5-dichlorotoluene was used in place of 3,4-dichlorotoluene in Example 1A and that the quantity of the iced water was increased to 1000 ml. As the result 24.1 g of crude DCTCT was obtained. BY gas chromatography the crude product was proved to contain 72.1 wt % (Yield 62.4%) of 2,5-dichloro-4-trichloromethyltoluene, referred to as DCTCT-(5), and 27.9 wt % (Yield 33.3%) of DCBM while unreacted dichlorotoluene was not detected. The crude DCTCT was dissolved in 50 ml of n-hexane to remove insoluble matter, and the filtrate was subjected to concentration under reduced pressure and distillation under reduced pressure to thereby obtain 11.5 g (0.0410 mol, yield 41.0%) of DCTCT-(5) which had a purity of 99.2% and a melting point of 41.6°-42.5° C. The structure of this compound was confirmed by MASS (M 276) and H-NMR (in CDCl$_3$, δ2.39 3H (CH$_3$) s, 7.40 1H (3-H) s, 8.13 1H (6-H) s).

As a second run of synthesis of DCTCT-(5), the first step of Example 1B (using 1,2-dichloroethane) was repeated except that 16.1 g (0.1 mol) of 2,5-dichlorotoluene was used in place of 3,4-dichlorotoluene in Example 1B. As the result 25.2 g of crude DCTCT-(5) (purity 78.8%, Yield 71.3%) was obtained. In this product unreacted dichlorotoluene was not detected, and only DCBM was detected as by-product.

24.1 g of the crude DCTCT obtained by the above first run and 10.0 g of hydrogen fluoride were subjected to reaction in the same manner as in Example 1A except that the reaction temperature was raised to 95°-102° C., and the reaction product was treated in the same manner. As the result 11.3 g (0.0483 mol, yield 77.3%) of 2,5-dichloro-4-trifluoromethyltoluene (purity 97.8%, boiling point 83°-85° C. at 6 mmHg), referred to as DCTFT-(5), was obtained. The structure of this compound was confirmed by MASS (M+228), H-NMR (in CDCl$_3$, δ2.35 3H (CH$_3$) s, 7.32 1H (3-H) s, 7.6 1H (6-H) s) and F-NMR (in CDCl$_3$, 63.1 ppm 3F (CF$_3$) s, standard substance was CFCl$_3$).

EXAMPLE 5

The first step of Example 1B (preparation of DCTCT using 1,2-dichloroethane) was repeated except that 16.1 g (0.1 mol) of 2,6-dichlorotoluene was used in place of 3,4-dichlorotoluene in Example 1A. As the result 26.0 g of crude DCTCT was obtained. BY as chromatography the crude product was proved to contain 88.4 wt %

(Yield 82.7%) of 2,6-dichloro-3-trichloromethyltoluene, referred to as DCTCT-(6), and 11.6 wt % (Yield 15.0%) of DCBM while unreacted dichlorotoluene was not detected.

In a 100 ml stainless steel autoclave, 26.0 g of the crude DCTCT obtained by the above process and 10.0 g of hydrogen fluoride were subjected to reaction in the same manner as in Example 1A except that the reaction temperature was raised to 95°–102° C., and the reaction product was treated in the same manner. As the result 16.6 g (0.0527 mol, Yield 87.8%) of 2,6-dichloro-3-trifluoromethyltoluene (purity 98.7%, boiling point 83°–85° C. at 8 mmHg), referred to as DCTFT-(6), was obtained. The structure of this compound was confirmed by MASS (M+228), H-NMR (in $CDCl_3$, $\delta 2.58$ 3H ($CH_3$) s. 7.33 1H (5H) s, 7.43 1H (4-H) s) and F-NMR (in $CDCl_3$, 62.8 ppm 3F ($CF_3$) s, standard substance was $CFCl_3$).

We claim:

1. A method preparing a dichlorotrifluoromethyltoluene, comprising the steps of:

reacting a dichlorotoluene with carbon tetrachloride in 1,2-dichloroethane in the presence of an aluminum halide to thereby obtain crude dichlorotrichloromethyltoluene; and then reacting said crude dichlorotrichloromethyltoluene with hydrogen fluoride.

2. A method according to claim 1, wherein the reaction between said crude dichlorotrichloromethyltoluene and hydrogen fluoride is carried out at a temperature in the range from 0° to 150° C. under a pressure in the range from 3 to 20 kg/cm2.

3. A method according to claim 2, wherein said temperature is in the range from room temperature to 100° C.

4. A method according to claim 2, wherein said pressure is in the range from 8 to 10 $kg/cm^2$.

5. A method according to claim I, wherein the quantity of said hydrogen fluoride is from 3.2 to 10 mols per 1 mol of said crude dichlorotrichloromethyltoluene.

6. A method according to claim 5, wherein said quantity of hydrogen fluoride is from 6 to mols.

* * * * *